United States Patent
Maack

(10) Patent No.: US 9,801,604 B2
(45) Date of Patent: Oct. 31, 2017

(54) SYSTEM FOR CONTROLLING AN X-RAY DETECTOR

(71) Applicant: KONINKLIJKE PHILIPS N.V., Eindhoven (NL)

(72) Inventor: Hanns-Ingo Maack, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/037,457

(22) PCT Filed: May 6, 2015

(86) PCT No.: PCT/EP2015/059887
§ 371 (c)(1),
(2) Date: May 18, 2016

(87) PCT Pub. No.: WO2015/173077
PCT Pub. Date: Nov. 19, 2015

(65) Prior Publication Data
US 2017/0049412 A1  Feb. 23, 2017

(30) Foreign Application Priority Data
May 16, 2014  (EP) .................................... 14168684

(51) Int. Cl.
*H05G 1/56* (2006.01)
*A61B 6/00* (2006.01)
*A61B 6/06* (2006.01)

(52) U.S. Cl.
CPC ................ *A61B 6/548* (2013.01); *A61B 6/06* (2013.01); *A61B 6/4266* (2013.01);
(Continued)

(58) Field of Classification Search
CPC ........... A61B 6/00; A61B 6/06; A61B 6/4266; A61B 6/4405; A61B 6/548; A61B 6/56;
(Continued)

(56) References Cited

U.S. PATENT DOCUMENTS 6,069,935 A * 5/2000 Schick .................. G01T 1/2018
348/E5.086
9,046,609 B2 * 6/2015 Chicchetti ............ A61B 6/4405
(Continued)

FOREIGN PATENT DOCUMENTS

DE   102005002983 A1   8/2006
WO   2006046206 A1   5/2006

*Primary Examiner* — Jurie Yun

(57) ABSTRACT

The present invention relates to a system (1) for controlling an X-ray detector (11) for detection of X-ray radiation, an X-ray imaging arrangement (3) comprising such system (1) and a method for controlling an X-ray detector (11) for detection of X-ray radiation. The system (1) for detection of X-ray radiation comprises a trigger device (12). The trigger device (12) is configured to be arranged remotely from the X-ray detector (11). The trigger device (12) is furthermore configured to be data-linked to the X-ray detector (11). The trigger device (12) is configured to determine a start of an X-ray exposure of an X-ray tube (2), to generate an activation signal and to communicate such signal the X-ray detector (11) to activate image detection.

14 Claims, 2 Drawing Sheets

(52) U.S. Cl.
CPC .......... *A61B 6/4405* (2013.01); *A61B 6/4411* (2013.01); *A61B 6/54* (2013.01); *A61B 6/542* (2013.01); *A61B 6/56* (2013.01); *A61B 6/4233* (2013.01)

(58) Field of Classification Search
CPC ........ G01N 23/00; G01N 23/04; G01N 23/08; G01N 23/083
USPC .......................................... 378/62, 98.8, 116
See application file for complete search history.

(56) References Cited

U.S. PATENT DOCUMENTS

| | | |
|---|---|---|
| 2006/0284602 A1 | 12/2006 | Spahn |
| 2007/0116348 A1 | 5/2007 | Jabri |
| 2007/0260134 A1 | 11/2007 | Serceki et al. |
| 2012/0076266 A1 | 3/2012 | Kim et al. |
| 2012/0082294 A1 | 4/2012 | Virshup et al. |
| 2012/0134474 A1 | 5/2012 | Duca et al. |
| 2013/0208860 A1 | 8/2013 | Sugizaki |
| 2013/0322599 A1 | 12/2013 | Watanabe |
| 2015/0146862 A1* | 5/2015 | Kim ...................... G01T 1/2018 378/91 |
| 2017/0143286 A1* | 5/2017 | Exelmans ................ A61B 6/54 |

* cited by examiner

SYSTEM FOR CONTROLLING AN X-RAY DETECTOR

CROSS-REFERENCE TO PRIOR APPLICATIONS

This application is the U.S. National Phase application under 35 U.S.C. §371 of International Application No. PCT/EP2015/059887, filed on May 6, 2015, which claims the benefit of European Patent Application No. 14168684.0, filed on May 16, 2014. These applications are hereby incorporated by reference herein.

FIELD OF THE INVENTION

The present invention relates to a system for controlling an X-ray detector for detection of X-ray radiation, an X-ray imaging arrangement comprising such system and a method for controlling an X-ray detector for detection of X-ray radiation.

BACKGROUND OF THE INVENTION

A radiation imaging system, for example, an X-ray imaging system as used in the medical field using X-rays is widely known. Such X-ray imaging system comprises an X-ray source for emitting X-rays to an object to be imaged, an X-ray detector for detecting X-ray radiation passing through the object, and a control device for controlling the operation of the X-ray source and the X-ray detector.

WO 2006/046206 A1 discloses a portable X-ray detector unit comprising a portable, hand-held X-ray detector i.e. a cassette having a plurality of exposure detection fields for measuring the level of radiation to which the object to be imaged is exposed. The portable X-ray detector incorporates automatic exposure control (AEC) for terminating X-ray radiation supply to the object upon determination that the level of X-ray exposure exceeds a predetermined threshold. A user-interface is provided to control the AEC.

DE 10 2005 002983 A1 discloses an X-ray detector system comprising a sensor for registering the start of an X-ray exposure, wherein the X-ray detector is activated in response to the output of said sensor.

US 2012/0082294 A1 discloses an X-ray system comprising a sensor configured to sense a condition that results from an operation of the X-ray tube, wherein the output of the sensor is communicated to an X-ray detection panel.

It has recently been proposed to introduce an exposure detection system wherein the X-ray detector itself can detect the beginning of an exposure of radiation to the object to be imaged. However, this system can be further improved. For example, in case a relatively small area is being exposed and/or a low exposure rate is applied, the X-ray detector may not properly detect the beginning of an X-ray exposure.

SUMMARY OF THE INVENTION

Hence, there may be a need to provide a system for controlling an X-ray detector for detection of X-ray radiation, which system is capable of more reliably detect the beginning of an X-ray exposure.

The object of the present invention is solved by the subject-matters of the independent claims, wherein further embodiments are incorporated in the dependent claims. It should be noted that the following described aspects of the invention also apply for the X-ray imaging arrangement comprising the system according to the invention as well as the method according to the invention.

According to the present invention, a system for controlling an X-ray detector for detection of X-ray radiation is presented. Such system comprises a trigger device. The trigger device is configured to be arranged remotely from the X-ray detector. The trigger device is furthermore configured to be data-linked to the X-ray detector. Herein data-linked means a connection between the trigger device and the detector, either wired or wirelessly, for communicating data. A wireless data-link may be realized via WiFi, LAN or the like. The trigger device is configured to determine a start of an X-ray exposure of an X-ray tube in response to detecting X-ray radiation emitted by said X-ray tube, to generate an activation signal and to communicate said activation signal to the X-ray detector to activate detection of X-ray radiation by said detector. The trigger device comprises a tilt sensor configured for measuring the orientation of the trigger device, wherein the trigger device is configured to select from a plurality of X-ray detectors an X-ray detector having a substantially matching orientation.

By providing the trigger device remotely from the detector, the trigger device allows for positioning relatively close to the X-ray tube. More specifically, the system according to the prevention enables positioning the trigger device with respect to the X-ray tube such that interference of other elements interacting with the X-ray radiation emitted from the X-ray tube is effectively prevented from. As a result the system according to the invention advantageously enables more reliably detecting the beginning of an X-ray exposure. The system according to the invention is of particular use in procedures that involve exposure of relatively small areas and/or use of relatively low dose. Therefore, the system according to the invention is particularly suitable for use in medical imaging. More specifically, the system allows for effective use in diagnostic as well as interventional clinical procedures.

The trigger device triggers the detector to detect X-ray radiation depending on the X-ray radiation emitted by the X-ray tube. Hence, the system according to the invention does not overlook the beginning of an X-ray procedure, and avoids X-ray exposure without acquiring an X-ray image.

If the trigger device and hence the tilt sensor is positioned in substantially horizontal orientation, the trigger device will communicate with an X-ray detector mounted underneath a patient table. If the trigger device and therefore the tilt sensor are positioned in a substantially vertical orientation, the trigger device will communicates with an X-ray detector mounted in a wall system. Therefore the system according to the invention advantageously enables automatic switching between X-ray detectors.

Optionally the system according to the invention can be fitted as a subsystem onto any X-ray system. More specifically, the system according to the invention is compatible with any X-ray tube, any X-ray detector and any X-ray voltage generator. In order to detect the beginning of an X-ray exposure, the system according to the invention does not rely on any electrical connection or other signal interface to any X-ray tube, any X-ray voltage generator, any X-ray detector or any other part of an X-ray system. This makes the system according to the invention ultra-mobile and compatible with any X-ray system in the world for "easy upgrade". Such ultra-mobility and compatibility is extremely useful if e.g. a patient cannot be positioned on an X-ray table.

In a further preferred embodiment of the system according to the invention, the trigger device is configured to be attachable to a tube unit, to a collimator of the X-ray tube, or to standardized connecting interface rails of said collimator. This embodiment advantageously guarantees the trigger device to be positioned as closely as possible to the X-ray tube, thereby enhancing the reliability of detecting the beginning of an X-ray exposure.

In a further preferred embodiment of the system according to the invention, the trigger device further configured to determine an end of an X-ray exposure by the X-ray tube, to generate a corresponding end signal and to communicate said end signal to the X-ray detector to stop detection of X-ray radiation by said detector.

In a further preferred embodiment of the system according to the invention, the trigger device comprises a dose area product (DAP) meter configured to measure X-ray radiation quantity data and to communicate said X-ray radiation quantity data to the X-ray detector. DAP is a quantity used in assessing radiation risk arising from X-ray diagnostic examinations and X-ray interventional procedures. DAP is defined as the absorbed dose multiplied by the area irradiated, and is expressed in gray square centimeters (Gy*cm$^2$). DAP can be stored in picture archiving and communications systems (PACS) to comply with regulations in Germany and other countries, which regulations require archiving DAP together with the respective X-ray images in aforementioned PACS. The X-ray radiation quantity data can be transferred to the PACS and/or the X-ray detector via an interface such as RS232, CAN or the like.

In a further preferred embodiment of the system according to the invention the system comprises a processing unit configured to assign, for storing purposes, X-ray radiation quantity data measured by the DAP to the X-ray radiation detected by the X-ray detector. This embodiment advantageously allows for combining X-ray radiation detected by the detector and X-ray radiation quantity data. This enables generating patient images with patient dose information.

In a further preferred embodiment of the system according to the invention, the trigger device comprises a status indicator configured to indicate at least one status parameter of the system. Herein the status parameter may be one of the group of "ready", "working", "finished", "out of order", and the like. The trigger device may receive status information from a processing unit or host PC. The status information may be used to indicate, for example via a light emitting display (LED), a status parameter of the system. Different from the X-ray detector, which may be completely covered by the patient prior to and during X-ray imaging, the trigger device is not obstructed and hence clearly visible. The trigger device therefore provides an optimal location for positioning for the status indicator.

In a further preferred embodiment of the system according to the invention, the trigger device is configured to be wirelessly data-linked to the X-ray detector. This embodiment is advantageous in that it increases flexibility of positioning the trigger device.

According to the present invention, also an X-ray imaging arrangement is presented. Such X-ray imaging arrangement comprises an X-ray tube for emitting X-ray radiation towards an object to be imaged, an X-ray detector for detection of X-ray radiation passing through the object, and the system for controlling the X-ray detector.

In a preferred embodiment of the X-ray imaging arrangement according to the invention, the system is configured to be remotely arranged from the X-ray tube.

According to the present invention, also a method for controlling an X-ray detector for detection of X-ray radiation is presented. The method comprises the following steps, not necessarily in this order:

a) providing a trigger device,
b) determining, by the trigger device, a start of an X-ray exposure by an X-ray tube,
c) generating an activation signal by the trigger device in response to detecting X-ray radiation emitted by the X-ray tube,
d) communicating said activation signal to the X-ray detector to activate X-ray radiation detection.

The trigger device is arranged remotely from the X-ray detector and is data-linked to said X-ray detector.

The method for detection of X-ray radiation may further comprise the following steps, not necessarily in this order:
e) determining an end of an X-ray exposure of an X-ray tube by the trigger device,
f) generating an end signal by the trigger device, and
g) communicating said end signal to the X-ray detector to stop X-ray radiation detection.

It shall be understood that the system, the X-ray imaging arrangement and the method according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
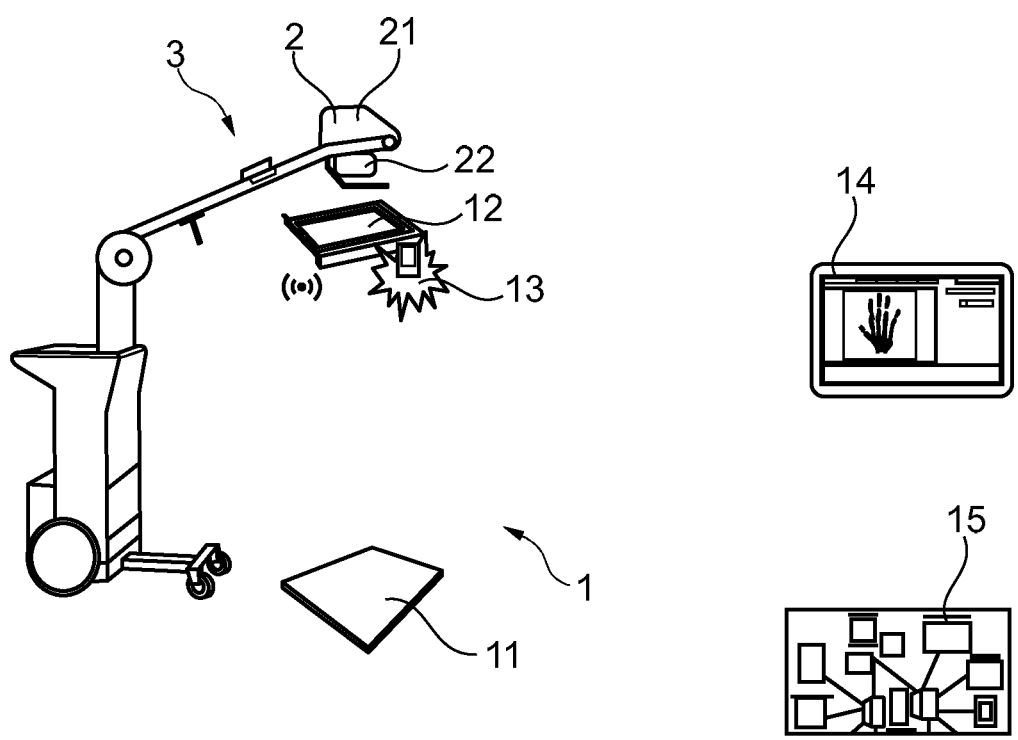
FIG. 1 shows a schematic drawing of an example of the system and the X-ray imaging arrangement according to the invention.

FIG. 1 shows schematically and exemplarily a system 1 for controlling an X-ray detector 11 for detection of X-ray radiation. The system comprises a trigger device 12. The trigger device is configured to be arranged remotely from to the X-ray detector 11. Furthermore the trigger device (12) is configured to be data-linked to the X-ray detector 11. The trigger device 12 is configured to determine a start of an X-ray exposure by an X-ray tube 2 in response to detecting X-ray radiation emitted by said X-ray tube 2, to generate an activation signal and to communicate said activation signal to the X-ray detector 11 to activate detection of X-ray radiation by said detector 11.

The X-ray detector 11 may comprise any type of X-ray sensitive element such as an array of digital X-ray sensor elements. The X-ray detector 11 may be a flat structure to be positioned also within narrow or small regions close to a patient.

In a specific example the X-ray detector 11 is portable and therefore may comprise a handle to facilitate a manual transportation.

FIG. 1 furthermore depicts schematically and exemplarily an X-ray imaging arrangement 3 comprising the X-ray tube 2 for emitting X-ray radiation towards an object to be imaged (not shown), the X-ray detector 11 for detection of X-ray radiation passing through the object, and the system 1 for controlling the X-ray detector for detection of X-ray radiation. The X-ray tube 2 can be mounted to an arm (as shown), to a ceiling suspension or else.

In a specific example the trigger device 12 is configured for wirelessly communicating data to the X-ray detector 11. In another example the trigger device 12 is configured for communicating directly with the X-ray detector 11. Consequently response times are reduced.

In a specific example the trigger device 12 is configured to be arranged at a location between an object to be imaged (not shown) and the X-ray tube 2. In another particular example the trigger device 12 is attached to a tube unit 21. Alternatively the trigger device 12 is attached to a collimator 22 of the X-ray tube 2 or to standardized connecting interface rails of said collimator 22. The collimator 22 is a device with lead plates used to define the size of an X-ray field.

In a specific example, the trigger device 12 is wirelessly data-linked to the X-ray detector 11. In another example, the trigger device 12 is also configured for determining an end of an X-ray exposure by the X-ray tube 2, generate a corresponding end signal and communicate said end signal to the X-ray detector 11 to stop X-ray radiation detection by the X ray detector 11.

In another specific example, the trigger device 12 comprises a dose area product (DAP) meter to measure X-ray radiation quantity data. In another specific example, DAP is subsequently stored in picture archiving and communications systems (PACS) 15 following the regulations in Germany and other countries.

In a specific example the trigger device is arranged for communicating the X-ray radiation quantity data or dose measured by the DAP meter directly to the X-ray detector 11 or to a processing unit 14. The processing unit 14 assigns the X-ray radiation quantity data to the X-ray radiation detected by the X-ray detector 11 for storing in the PACS 15.

In a specific example, the processing unit 14 is connected to a Radiology Information System (RIS). Such RIS provides a list of patients to be examined and patient demographic data which are later attached to the images and sent to the PACS 15. The processing unit 14 receives X-ray radiation detected by the X-ray detector 11 and processes such X-ray radiation. The processing unit 14 is configured for image pre- and post-processing. The processing unit 14 receives the measured dose information from the DAP meter. The processing unit 14 is configured to save the data and/or to be further connected to the PACS 15 to upload the images together with the patient demographics.

In a specific example, the trigger device 12 further comprises a status indicator 13 to indicate status parameters of the system 1. The trigger device 12 receives status information from the processing unit 14. In this specific example the status indicator 13 is a ready indicator in the form of a LED attached to the trigger device 12. The LED may be green for "ready", which means the X-ray detector 11 is ready for operation, or red for "not ready", which means the X-ray detector 11 is not ready for operation.

In a specific example the trigger device 12 further comprises an integrated tilt sensor (not shown) for measuring the orientation of the trigger device 12, wherein the trigger device 12 is configured to select from a plurality of X-ray detectors (not shown) the X-ray detector 11 having a substantially matching orientation.

In another example, the trigger device 12 may further comprise an accurate watch to provide X-ray exposure data with a time stamp.

In a specific example all data transfer between the trigger device 12 and the X-ray detector 11, the processing unit 14, and the PACS 15 occurs wirelessly via e.g. WiFi, LAN or the like. However, there is no data connection between the X-ray tube 2 and the trigger device 12 and/or the processing unit 14.

The system 1 may be driven by line voltage, batteries, accumulators or the like.

The basic principle of the system 1, arrangement 3 and the method for controlling an X-ray detector for detection of X-ray radiation is also suitable for other radiation than X-ray, other imaging purposes than medical imaging, and other medical purposes than imaging.

Figure 2:
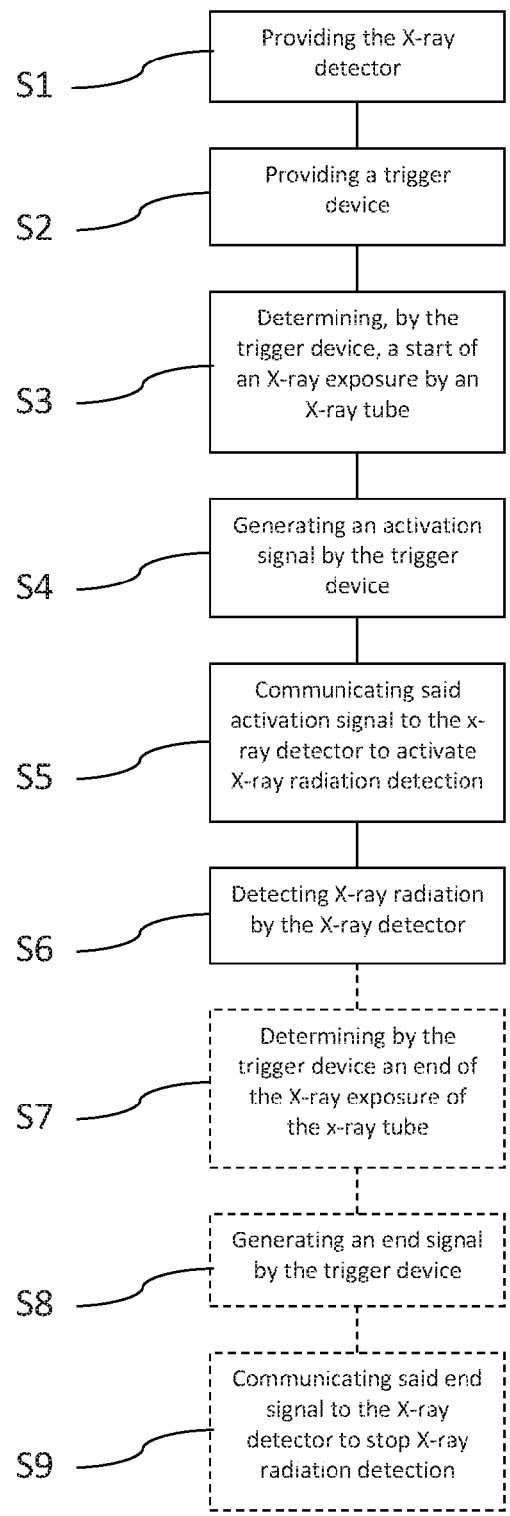
FIG. 2 shows a schematic overview of steps of a method for controlling an X-ray detector for detection of X-ray radiation.

FIG. 2 shows a schematic overview of steps of a method for controlling an X-ray detector 11 for detection of X-ray radiation. The method comprises the following steps, not necessarily in this order:

a step S2 for providing a trigger device 12, a step S3 for determining, by the trigger device 12, a start of an X-ray exposure by an X-ray tube 2, a step S4 for generating an activation signal by the trigger device 12, and a step S5 for communicating said activation signal to the X-ray detector 11 to activate X-ray radiation detection.

The trigger device 12 is arranged remotely from to the X-ray detector 11 and is data-linked to the X-ray detector 11. In an example, the method comprises a step S1 for providing the X-ray detector 11. In another example, the method comprises a step S6 for detecting X-ray radiation by the X-ray detector 11. In another example the method comprises the following steps, not necessarily in this order a step S7 for determining, by the trigger device 12, an end of an X-ray exposure of the X-ray tube 2, a step S8 for generating an end signal by the trigger device 12, and a step S9 for communicating said end signal to the X-ray detector 11 to stop X-ray radiation detection.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. System for controlling an X-ray detector for detection of X-ray radiation, comprising a trigger device, wherein the trigger device is configured to be arranged remotely from the X-ray detector; wherein the trigger device is configured to be data-linked to the X-ray detector; wherein the trigger device is configured to determine a start of an X-ray exposure by an X-ray tube in response to detecting X-ray radiation emitted by said X-ray tube, to generate an activation signal and to communicate said activation signal to the X-ray detector to activate detection of X-ray radiation by said detector; and wherein the trigger device comprises a tilt sensor configured for measuring the orientation of the trigger device, wherein the trigger device is configured to select from a plurality of X-ray detectors an X-ray detector having a substantially matching orientation.

2. System according to claim 1, wherein the trigger device is further configured to determine an end of an X-ray exposure by the X-ray tube, to generate an end signal and to communicate said end signal to the X-ray detector to stop detection of X-ray radiation by said detector.

3. System according to claim 1, wherein the trigger device is a dose area product meter configured to measure an X-ray radiation quantity data and to communicate said X-ray radiation quantity data to the X-ray detector.

4. System according to claim 3, further comprising a processing unit configured to assign the X-ray radiation quantity data measured by the dose area product meter to the X-ray radiation detected by the X-ray detector for storing purposes.

5. System according to claim 1, wherein the trigger device comprises a status indicator configured to indicate at least one status parameter of the system.

6. System according to claim 5, wherein the trigger device is configured to be wirelessly data-linked to the X-ray detector.

7. System according to claim 6, wherein the trigger device is configured to communicate directly with the X-ray detector.

8. System according to claim 7, wherein the trigger device is configured to be arranged at a location between an object to be examined and the X-ray tube.

9. System according to claim 1, wherein the trigger device is configured to be attachable to a tube unit, to a collimator of the X-ray tube, or to connecting interface rails of said collimator.

10. System according to claim 1, wherein the system is portable.

11. An X-ray imaging arrangement, comprising an X-ray tube for emitting X-ray radiation towards an object to be imaged, an X-ray detector for detection of X-ray radiation passing through the object, and the system for controlling the X-ray detector for detection of X-ray radiation according to claim 1.

12. An X-ray imaging arrangement according to claim 1, wherein the system is configured to be remotely arranged from the X-ray tube.

13. A method for controlling an X-ray detector for detection of X-ray radiation in medical imaging, comprising the following steps:
providing a trigger device,
providing, in the trigger device, a tilt sensor configured for measuring the orientation of the trigger device,
determining, by the trigger device, a start of an X-ray exposure by an X-ray tube in response to detecting, by the trigger device, X-ray radiation emitted by said X-ray tube,
generating an activation signal,
selecting from a plurality of X-ray detectors an X-ray detector having an orientation substantially matching the orientation of the trigger device,
communicating the activation signal to the X-ray detector to activate X-ray radiation detection,
wherein the trigger device is arranged remotely from the X-ray detector and is data-linked to the X-ray detector.

14. A method according to claim 13, further comprising the step of
determining, by the trigger device, an end of an X-ray exposure of an X-ray tube,
generating an end signal by the trigger device, and
communicating said end signal to the X-ray detector to stop X-ray radiation detection.

* * * * *